(12) United States Patent
Berg et al.

(10) Patent No.: US 8,367,079 B2
(45) Date of Patent: Feb. 5, 2013

(54) LIQUID PRESERVATIVE COMPOSITIONS

(75) Inventors: Kenneth R. Berg, St. John, IN (US); Teresa Germain, Orland Park, IL (US)

(73) Assignee: Rhodia Operations (FR)

( * ) Notice: Subject to any disclaimer, the term of this patent is extended or adjusted under 35 U.S.C. 154(b) by 179 days.

(21) Appl. No.: 12/812,063

(22) PCT Filed: Jan. 23, 2009

(86) PCT No.: PCT/US2009/000460
§ 371 (c)(1),
(2), (4) Date: Jul. 8, 2010

(87) PCT Pub. No.: WO2009/094198
PCT Pub. Date: Jul. 30, 2009

(65) Prior Publication Data
US 2010/0286218 A1    Nov. 11, 2010

Related U.S. Application Data

(60) Provisional application No. 61/062,356, filed on Jan. 25, 2008.

(51) Int. Cl.
*A61K 9/00* (2006.01)
(52) U.S. Cl. .......................... 424/400; 252/380
(58) Field of Classification Search .............. 424/400
See application file for complete search history.

(56) References Cited

U.S. PATENT DOCUMENTS

| 5,100,656 A * | 3/1992 | Lang et al. ............. 424/70.19 |
| 5,863,546 A * | 1/1999 | Swinehart ................ 424/401 |
| 2006/0093634 A1 | 5/2006 | Lutz et al. |
| 2007/0265352 A1 | 11/2007 | Roeding et al. |

FOREIGN PATENT DOCUMENTS

| EP | 0 559 319 A2 | 9/1993 |
| EP | 0 659 404 A2 | 6/1995 |
| EP | 1 541 124 A1 | 6/2005 |
| EP | 2 138 189 A1 | 12/2009 |

OTHER PUBLICATIONS

Cosmetics Unmasked (http://www.gina.antczak.btinternet.co.uk/CU/IE-G.HTM; 2002).*
Routledge et al. (Toxicol. Appl. Pharmacol. 153, 12-19. (1998)).*
Alexander (Contact Dermatitis 2002, 46, 191-196).*
Friberg et al. (Ind. Eng. Chem. Res. 1996, 35, 2856-2859).*

* cited by examiner

*Primary Examiner* — Robert A Wax
*Assistant Examiner* — Devang Thakor
(74) *Attorney, Agent, or Firm* — Olson & Cepuritis, Ltd.

(57) ABSTRACT

A liquid preservative composition comprises (a) an alkanol fatty monoester; and (b) an aqueous isothiazolinone solution, an alkanol-substituted aromatic compound, or a combination thereof; and is free from formaldehyde, formaldehyde-releasing compounds, and paraben compounds. Preferred compositions comprise glyceryl caprylate, together with either phenethyl alcohol or an aqueous 2-methyl-4-isothiazolin-3-one solution.

21 Claims, No Drawings

LIQUID PRESERVATIVE COMPOSITIONS

FIELD OF THE INVENTION

This invention relates to preservative compositions. More particularly, this invention relates to liquid preservative compositions containing alkanol fatty monoesters that are free from formaldehyde, formaldehyde-releasing compounds, phenolic compounds, and paraben compounds.

BACKGROUND OF THE INVENTION

It is widely known that there is a growing demand for personal care and cosmetic products that are free from certain components perceived to be potentially harmful, which are found in many common preservative (i.e., antimicrobial) compositions. In particular, there is a strong demand in the marketplace for use in consumer and industrial products generally for alternatives to common preservative materials such as formaldehyde-releasing compounds (due to the known hazards of formaldehyde), phenolic compounds, certain paraben compounds (i.e., para-hydroxybenzoate esters), and certain halogenated compounds.

Known alternatives to such compounds are the fatty glyceryl monoester materials developed by Kabara, such as glyceryl laurate, glyceryl caprylate, and the like. These high monoester-containing materials tend to have relatively weak antimicrobial activity compared to traditional preservatives, however. In addition, many of the monoesters are solids at room temperature, and may require excessive heating to incorporate them into cosmetic or personal care products. The use of heat to dissolve or admix components in cosmetic and personal care product manufacturing processes can lead to undesirable side reactions, degradation of key ingredients, and discoloration in some cases, and is uneconomically energy intensive.

There is an ongoing need for new liquid preservative compositions for use in cosmetics and personal care products, especially, which are free from formaldehyde, formaldehyde-releasing compounds, phenolic compounds, paraben compounds, and preferably free from halogenated compounds, while still maintaining a broad spectrum of antimicrobial activity, and which can be formulated into personal care and cosmetic products without undue heating. The present invention fulfills these needs.

SUMMARY OF THE INVENTION

The present invention provides liquid preservative compositions, which comprise an alkanol fatty monoester and are free from formaldehyde, formaldehyde-releasing preservatives, phenolic preservatives, and paraben-type preservatives. A liquid preservative composition of the invention also comprises an aqueous isothiazolinone solution, an alkanol-substituted aromatic compound, or a combination thereof, in addition to the alkanol fatty monoester. Preferably, the preservative compositions of the invention are also free from halogenated compounds.

The liquid preservative compositions of the invention are pourable, pumpable liquids, which provide a broad spectrum of protection against a variety of bacteria and fungi species. A preferred liquid preservative composition of the invention comprises glyceryl caprylate in combination with either phenethyl alcohol or an aqueous solution of 2-methyl-4-isothiazolin-3-one or both. Such compositions provide a surprisingly enhanced activity against *Candida albicans* compared to glyceryl caprylate, phenethyl alcohol, or aqueous 2-methyl-4-isothiazolin-3-one solution, when used as the sole preservative.

The liquid nature of the preservative composition of the invention facilitates efficient mixing of the preservative composition with other cosmetic or industrial ingredients without heating.

DETAILED DESCRIPTION OF PREFERRED EMBODIMENTS

The liquid preservative compositions of the present invention comprise an alkanol fatty monoester (i.e., an alkanol monoester of a $C_8$-$C_{22}$ alkanoic acid) together with an alkanol-substituted aromatic compound, an aqueous isothiazolinone solution, or a combination thereof.

As used herein and in the appended claims, the terms "alkanol fatty monoester" and "alkanol monoester of a $C_8$-$C_{22}$ alkanoic acid" are synonymous with one another and refer to monoesters of a diol or polyol with a $C_8$-$C_{22}$ carboxylic acid moiety. An alkanol fatty monoester for use in the compositions of the invention can comprise a single ester compound or a combination of two or more esters. For example, the alkanol fatty monoester can comprise a monoester of a glycol or glycerin with a single carboxylic acid (e.g., caprylic acid) or with a combination of carboxylic acids, such as are often obtained by hydrolysis of natural oils. Preferred alkanol fatty monoesters are glycerin fatty acid monoesters. Particularly preferred alkanol fatty monoesters are glyceryl caprylate (i.e., glyceryl monooctanoate) and glyceryl caprate (i.e., glyceryl monodecanoate), which are commercially available from a variety of sources. Typically, alkanol fatty monoesters are prepared by direct reaction of a polyol with a fatty carboxylic acid. Alternatively, such mono esters can be prepared by transesterification of a fatty ester (e.g., a fatty methyl ester) with a polyol. Alkanol fatty monoesters useful in the practice of the present invention can be prepared by any suitable means.

The term "alkanol-substituted aromatic compound" as used herein and in the appended claims refers to an aromatic compound (e.g., a phenyl or naphthyl compound) bearing at least one alkanol substituent. Alkanol substituents are alkyl or alkoxy moieties that bear a hydroxyl group, such as hydroxyethyl, hydroxymethyl or 2-hydroxyethoxy substituents. Preferred alkanol-substituted aromatic compounds for use in the present invention include, phenoxyethanol, and benzyl alcohol, and particularly phenethyl alcohol.

The term "isothiazolinone solution" as used herein and in the appended claims refers to aqueous solutions of compounds comprising a 4-isothiazolin-3-one base structure, and preferably including a 2-methyl (i.e., N-methyl) substituent, at an active concentration of about 0.005 to about 55 weight %, preferably of about 0.1 to about 25 weight %, more preferably of about 1 to about 10 weight %. The isothiazolinone compound can optionally include a 5-chloro substituent, as well. The term "isothiazolinone solution" includes aqueous solutions of individual compounds, such as 2-methyl-4-isothiazolin-3-one, as well as mixtures of compounds, such as a mixture of 5-chloro-2-methyl-4-isothiazolin-3-one and 2-methyl-4-isothiazolin-3-one, and the like. Aqueous isothiazolinone solutions optionally include a water-soluble inorganic salt, such as magnesium nitrate in an amount of up to about 25 weight %.

Particularly preferred is 2-methyl-4-isothiazolin-3-one (CAS No. 2682-20-4), preferably free from halogenated compounds. Aqueous 2-methyl-4-isothiazolin-3-one solutions are commercially available at a reported active concentration of 9.5-9.9% in water sold under the brand names NEOLONE® 950 Preservative by Rohm and Haas Company; and MICROCARE® MT by Thor Products; and at a reported active concentration of 50-52% in water sold under the brand name KORDEK® LX5000 Industrial Microbiocide by Rohm and Haas Company.

The alkanol fatty monoester preferably constitutes about 5 to about 99.9 percent by weight, more preferably about 5 to about 95 percent by weight, of the liquid preservative composition. In one preferred embodiment, the liquid preservative composition comprises about 85 to about 95 percent by weight of the alkanol fatty monoester (e.g., about 90 percent by weight glyceryl caprylate), and about 0.5 to about 2 active percent by weight of isothiazolinone (e.g., about 10 weight percent of an aqueous solution of about 9 to about 10 active percent by weight 2-methyl-4-isothiazolin-3-one). Another preferred composition of the invention comprises about 35 to about 60 percent by weight of the alkanol fatty monoester (e.g., about 40 percent by weight glyceryl caprylate), and about 40 to about 65 percent by weight of an alkanol-substituted aromatic compound (e.g., about 60 percent by weight phenethyl alcohol).

The preservative compositions of the present invention provide a variety of desirable features for use in consumer products, such as cosmetics and personal care products, including emolliency (i.e., due to the alkanol fatty monoester component) and surprisingly unexpected broad spectrum antimicrobial activity. The compositions of the present invention provide surprisingly enhanced activity against *Candida albicans* compared to preservatives that include an alkanol fatty monoester alone, an alkanol-substituted aromatic compound alone, or an aqueous isothiazolinone solution alone. In addition, compositions that include phenethyl alcohol also provide a desirable fragrance characteristic. The presence in the liquid preservative composition of the alkanol-substituted aromatic compound and/or an aqueous isothiazolinone solution (e.g., about 8 to about 12 weight percent of an aqueous solution of about 9 to about 10 active weight percent 2-methyl-4-isothiazolin-3-one) also liquefies the normally solid alkanol fatty monoester. This liquefying characteristic allows highly concentrated, alkanol fatty monoester preservative compositions to be prepared, which are pumpable and pourable without requiring the addition of large amounts of solvents that do not contribute to the preservative activity of the compositions.

The preservative compositions of the invention are free from formaldehyde, formaldehyde-releasing compounds, phenolic compounds, and paraben compounds. Preferably, the compositions are free from halogenated preservatives, as well. In some preferred embodiments, the compositions of the invention are non-aqueous or contain relatively small amounts of water (e.g., less than about 15 percent by weight, or preferably less than about 10 percent by weight water) mainly derived from the aqueous isothiazolinone solution, when present.

As disclosed herein, the liquid preservative concentrates typically can be admixed with other ingredients of consumer products, such as cosmetic and personal care products, or industrial products in an energy conserving manner with minimal or no heating, which is an added advantage of the compositions of the present invention. The use of the terms "cosmetic" and "personal care" products, and grammatical variations thereof, individually or collectively, is intended to encompass topically applied toiletries, health care, beauty aids, over-the-counter pharmaceutical formulations, and the like. The term "industrial" products is intended to encompass products used in institutional, industrial, or household environments, for cleaning and maintaining the facility.

Another aspect of the present invention is a method of preserving a consumer or industrial product comprising admixing a preservative effective amount of a liquid preservative composition of the invention with a consumer or industrial product. In a preferred embodiment, the preservative effective amount of the preservative composition is in the range of about 0.1 to about 35 percent by weight based on the combined weight of the preservative and the consumer or industrial product.

Yet another preferred aspect of the present invention is a cosmetic or personal care product comprising about 0.1 to about 25 percent by weight glyceryl caprylate in combination with about 0.02 to about 10 percent by weight phenethyl alcohol and/or an aqueous solution of about 2 to about 200 ppm (actives basis) of 2-methyl-4-isothiazolin-3-one; the product being free from formaldehyde, formaldehyde-releasing compounds, phenolic compounds and paraben compounds, and preferably is free from halogenated preservatives.

The preservative composition of the present invention can be employed in aqueous or non-aqueous liquid products, including emulsions of oil-in-water, water-in-oil, and multiple phase emulsions.

The following examples are provided to illustrate preferred embodiments of the present invention, and are not meant to limit the scope of the invention.

EXAMPLE 1

Evaluation of Broad Spectrum Preservative Activity in a Cleansing Composition

Several 200-gram samples of a cleanser base were admixed with a variety of preservative compositions, and challenged with selected bacteria and fungi (*Escherichia coli, Pseudomonas aeruginosa, Staphylococcus aureus, Aspergillus niger,* and *Candida albicans*) according to the following procedure:

About 0.5 mL of an aqueous suspension containing about $1 \times 10^6$ to about $2 \times 10^7$ colony forming units-per-milliliter (cfu/mL) of *Aspergillus niger* in a pH 7.2 phosphate buffer was transferred to a tube containing about 9.5 mL of a sample of a cleanser base composition to provide an inoculum level of about $1 \times 10^5$ to about $1 \times 10^6$ cfu/mL. The same procedure was used to challenge samples of the cleanser base with *Candida albicans* and with a mixed culture of *Escherichia coli, Pseudomonas aeruginosa,* and *Staphylococcus aureus,* at about the same inoculum levels. The challenged samples were stored at an ambient room temperature of about 22° C. At 7 days and 14 days after challenge, aliquots from each sample were diluted according to the following procedure: about 1 mL of each challenged sample was aseptically transferred into a tube containing about 9 mL of Dey/Engley (D/E) neutralizing broth with thorough mixing to provide a dilution ratio of about 1:10. About 0.1 mL of each of the 1:10 diluted samples was then aseptically transferred into separate tubes, each tube containing about 9 mL of sterile buffered saline solution, (3.5 g/L phosphoric acid in 0.9 wt. % NaCl solution, adjusted to pH 7.2 with 50 wt. % aqueous sodium hydroxide), with thorough mixing, to provide a dilution ratio of about 1:1000.

Finally, each of the 1:10 diluted samples and each of the 1:1000 diluted samples were plated according to the following procedure: about 1 mL of each of the diluted samples was plated with Letheen agar (bacteria samples) or Sabouraud dextrose agar (yeast and mold samples). The Letheen agar plates were incubated at 35±2° C. for about 48 hours (about 2 days) in an inverted position, and the resulting microbial colonies were counted. The Sabouraud dextrose agar plates were incubated at 25±2° C. for about 120 hours (about 5 days) in an upright position and the resulting microbial colonies were counted.

The formulations of the cleanser base and the D/E Neutralizing Broth used in these evaluations are provided in Table 1 and Table 2, respectively. The preservative compositions and observed plate counts (in cfu) are shown in Tables 3 and 4.

TABLE 1

Cleanser Base Formulation.

| Component (Common or INCI* Name) | Weight % |
|---|---|
| Water to 100 weight % | q.s. |
| PEG-80 sorbitan laurate | 5 |
| PEG-6000 distearate | 1.1 |
| Sodium lauroamphoacetate (44% solids in water) | 2 |
| Sodium laureth sulfate (70% solids in water) | 3.7 |
| Cocamidopropyl betaine (44% solids in water) | 6.4 |
| Citric acid (25% aq.) to pH 6.7 | q.s. |

*INCI = International Nomenclature Cosmetic Ingredient name assigned by the International Committee of the Personal Care Products Council (formerly Cosmetic, Toiletry, and Fragrance Association (CTFA)).
q.s. = quantity sufficient

TABLE 2

D/E Neutralizing Broth Formulation.

| Component (Common or INCI Name) | Grams/Liter Water |
|---|---|
| Pancreatic digest of casein | 5 |
| Yeast extract | 2.5 |
| Dextrose | 10 |
| Sodium thioglycolate | 1 |
| Sodium thiosulfate | 6 |
| Sodium bisulfite | 2.5 |
| Polysorbate 80 | 5 |
| Lecithin | 7 |
| Bromcresol purple | 0.02 |

TABLE 3

Day-7 Plate Counts (cfu).

| Ex. | Preservative added (wt. % or ppm) * | EC | PA | SA | AN | CA |
|---|---|---|---|---|---|---|
| A | 0.9% phenoxyethanol (POE) | <10 | 1500 | 18500 | <10 | 9500 |
| B | 95 ppm 2-methyl-4-isothiazolin-3-one (MI) | 155 | 115 | 215 | 1000 | 10500 |
| C | 0.5% glyceryl caprylate (GC) | 15 | 7500 | <10 | 1000 | 500 |
| D | 0.5% phenethyl alcohol (PEA) | 380 | 10 | 7500 | 25 | 91000 |
| E | 0.15% sodium benzoate | TN | TN | 9000 | 1500 | 336500 |
| F | none | TN | TN | 13500 | 2500 | TN |
| G | 95 ppm MI and 0.5% GC ** | <10 | 1000 | 10 | <10 | <10 |
| H | 0.5% PEA and 0.5% GC *** | <10 | 9500 | <10 | 10 | <10 |

* Amount added to the base composition.
** Representative of an example of the Invention for amounts obtainable by adding to the base composition e.g., 0.56% by weight of a liquid preservative composition containing about 90 wt. % glyceryl caprylate, about 1.7 active wt. % MI and about 8.3 wt % water.
*** Representative of an example of the Invention for amounts obtainable by adding to the base composition e.g., 1% by weight of a liquid preservative composition containing 50 wt. % glyceryl caprylate and 50 wt. % PEA.
EC = *Escherichia coli*; PA = *Pseudomonas aeruginosa*; SA = *Staphylococcus aureus*; AN = *Aspergillus niger*; CA = *Candida albicans*. TN = too numerous to count

TABLE 4

Day-14 Plate Counts (cfu).

| Ex. | Preservative added (wt. % or ppm) | EC | PA | SA | AN | CA |
|---|---|---|---|---|---|---|
| A | 0.9% phenoxyethanol (POE) | <10 | <10 | 100 | <10 | <10 |
| B | 95 ppm 2-methyl-4-isothiazolin-3-one (MI) | 10 | <10 | 6500 | 500 | 15000 |
| C | 0.5% glyceryl caprylate (GC) | 10 | 117500 | 1000 | 280 | 485 |
| D | 0.5% phenethyl alcohol (PEA) | 1000 | 1000 | 1000 | <10 | 2000 |
| E | 0.15% sodium benzoate | TN | TN | 500 | 3500 | TN |
| F | none | TN | TN | 1000 | 6500 | TN |
| G | 95 ppm MI and 0.5% GC | <10 | <10 | 1000 | <10 | <10 |
| H | 0.5% PEA and 0.5% GC | <10 | 900 | 500 | <10 | <10 |

The data in Tables 3 and 4 clearly indicate that the preservative compositions of the invention (Examples G and H) exhibited desirably good activity in the cleanser base against the various bacteria and yeast species tested, as well as a surprisingly and unexpectedly improved activity against *Candida albicans* compared to the preservatives that included glyceryl caprylate alone (Ex. C), phenethyl alcohol alone (Ex. D), and 2-methyl-4-isothiazolin-3-one alone (Ex. B). In addition, the antimicrobial activities of the compositions of the invention were comparable to or superior to various other known formaldehyde-free and paraben-free preservatives (i.e., Examples A and E) for most or all of the tested microbial species. The compositions of the invention met or exceeded the standard United States Pharmacopeia (USP) requirement for antimicrobial effectiveness, having reduced bacterial levels by a minimum of one log level in seven days and having reduced bacterial levels by three or more log levels in 14 days, and showing no increase over the initial inoculum level of fungi at any time during the test.

EXAMPLE 2

Evaluation of Preservative Activity by Minimum Inhibitory Concentration

A Minimum Inhibitory Concentration (MIC) evaluation was conducted for five preservative liquids; i.e., Ex. A: an aqueous liquid preservative composition of the invention comprising about 90 weight % glyceryl caprylate (GC), and about 1 active weight % 2-methyl-4-isothiazolin-3-one (MI) with the balance being water (GCM); Ex. B: a liquid preservative composition of the invention comprising about 60 weight % PEA and about 40 weight % GC (GCP); as well as the individual components: i.e., Ex. C: glyceryl caprylate (GC); Ex. D: an aqueous 2-methyl-4-isothiazolin-3-one (MI) solution of about 9.5% active MI; and Ex. E: phenethyl alcohol (PEA). In this evaluation, nutrient broth solutions were made with different concentrations of the test compounds, and then all the solutions were spiked with the same concentration of test organism. Growth was indicated by a solution becoming hazy after 24 hours of incubation time. The highest dilution without observable growth is the Minimal Inhibitory Concentration (MIC).

Procedures:

The following procedure was adopted from the *Manual of Clinical Microbiology*, 2nd Ed. published by the American Society for Microbiology, ISBN 0-914826-00-X.

Growth Media:

Prepare and sterilize Mueller-Hinton Broth (MH broth) (Fluka) per the manufacturer's instructions (dissolve 23 grams in one liter water and autoclave at 121° C. for 15 minutes minimum).

Dilution of Antimicrobial Agent:

The stock antimicrobial solution is diluted (in MH broth) to twice the highest final test concentration desired. Sterile 13×100 mm screw-capped culture tubes are used. Two-fold dilutions are made directly in the tubes. To the first tube is added 2 mL of the working solution of antimicrobial agent. To each remaining tube is added 1 mL of broth. Using aseptic technique, an amount of 1 mL is transferred from the first tube to the second tube and is thoroughly mixed. After thorough mixing, 1 mL is transferred from the second tube to the third tube. This process is repeated through the second to last tube, from which 1 mL is removed and discarded. The final tube receives no antimicrobial agent and serves as a growth control.

Preparation of Inoculums:

Reagents

Buffered saline (3.5 g/L phosphoric acid in a 0.9% NaCl solution, pH adjusted to 7.2 with 50 wt. % aqueous NaOH, sterilized by autoclave).

The organisms used were:

S. aureus 6538 EPWR E7 (Fisher cat#23-003-378)

P. aeruginosa 9027 EPWR E7 (Fisher cat#23-003-377)

A. niger 16404 E PWR 10PK (Fisher cat#23-003-3397)

The organisms are preferably lyophilized Microbiologics $E^{power}$ E7 microorganisms (mean assay value of between 10 million and 100 million colony forming units or equivalent concentration). The final concentrations of the microorganism in the inoculum should be in the order of $10^6$-$10^7$ cfu/mL.

Organism Hydration:

1. Allow unopened vial of microorganism pellets to equilibrate to room temperature.

2. Warm 1 tube of 10 mL buffered saline per organism used to about 35-37° C.

3. Using sterile forceps, transfer 2 pellets to the saline and return unused pellets to storage.

4. Incubate the hydrated material at about 35-37° C. for about 30 minutes.

5. Vortex the vials until homogeneous.

6. Add 1.0 ml of the diluted culture suspension to each of the previously prepared tubes containing the preservative compositions. The final concentration of preservative is now one-half of the original concentration in each tube.

All tubes were incubated at about 35° C. for about 24 hours. The tubes were then examined for visible signs of bacterial growth. The highest concentration without observed growth was recorded as the observed MIC values and are shown in Table 5.

TABLE 5

| | | MIC Values, (%) | | |
|---|---|---|---|---|
| Ex. | Preservative | A. niger | P. aeruginosa | S. aureus |
| A | GCM | 0.19 | 0.25 | 0.125 |
| B | GCP | 1.0 | 0.63 | 0.63 |
| C | GC | 2.0 | 1.0 | 1.0 |
| D | MI | 0.1 | 0.008 | 0.1 |
| E | PEA | 1.0 | 0.9 | 0.9 |

The MIC values from Table 5 were then used to calculate the Fractional Inhibitory Concentration Index (FICI) (sometimes called the Synergy Index) of GCM and GCP versus the various individual test organisms using the following equation.

$$FICI=(MICa/MICA)+(MICb/MICB)$$

Where:

MICa=concentration of component A at the MIC of the combination of A & B;

MICA=MIC of component A alone;

MICb=concentration of component B at the MIC of the combination of A & B; and

MICB=MIC of component B alone.

A description of the FICI is provided in an article by Greene et al., entitled "Synergistic Inhibition of Microbial Sulfide Production by Combinations of the Metabolic Inhibitor Nitrite and Biocides", *Applied and Environmental Microbiology*, 72, 7897-7901 (2006), the disclosures of which are incorporated herein by reference.

The FICI equation is equivalent to what is commonly referred to as the Synergy Index measurement published in a paper by Kull et al., entitled "Mixtures of Quaternary Ammonium Compounds and Long-chain Fatty Acids as Antifungal Agents", in *Applied Microbiology*, V9, 538-541 (1961), and discussed in the articles by Steinberg, "Measuring Synergy", *Cosmetics & Toiletries®*, 115, 59-62 (2000) and by Schmaus et al. "1,2-Alkanediols for Cosmetic Preservation", *Cosmetics & Toiletries®*, 123, 53-64 (2008), the disclosures of which are incorporated herein by reference. The calculated FICI values are provided in Table 6.

TABLE 6

Fractional Inhibitory Concentration Index

| Ex. | Preservative | A. niger | P. aeruginosa | S. aureus |
|-----|--------------|----------|---------------|-----------|
| A | GCM | 0.1 | 0.5 | 0.1 |
| B | GCP | 0.8 | 0.7 | 0.7 |

A Fractional Inhibitory Calculated Index of less than 1.0 indicates synergistic action between the two components. Values of 0.5 or less indicate strong synergistic action between the two components. Values between 0.5 and 1.0 are indicative of mild synergy.

The results in Table 6 clearly indicate an unexpected synergy for GCP against all the organisms tested in this example. GCM exhibited a surprisingly strong synergy against all test organisms.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A pourable, pumpable, liquid preservative composition in the form of a liquified concentrate of antimicrobial material consisting of the following components (a) and (b):

(a) an alkanol fatty monoester; and
(b) an effective liquifying amount of a material selected from the group consisting of an aqueous isothiazolinone solution, an alkanol-substituted aromatic compound, and a combination thereof; and wherein, less than about 15% water, on a total composition weight basis is derived from the aqueous isothiazolinone, when present;

wherein the preservative composition is free from formaldehyde, formaldehyde-releasing compounds, phenolic compounds, halogenated compounds, and paraben compounds; and is pourable and pumpable.

2. The liquid preservative composition of claim 1 wherein the alkanol fatty monoester is a monoester of glycerin with a $C_8$-$C_{22}$ alkanoic acid moiety.

3. The liquid preservative composition of claim 1 wherein the alkanol fatty monoester is a monoester of a glycol with a $C_8$-$C_{22}$ alkanoic acid moiety.

4. The liquid preservative composition of claim 1 wherein the alkanol fatty monoester is a monoester of a diol with a $C_8$-$C_{22}$ alkanoic acid moiety.

5. The liquid preservative composition of claim 1 wherein the alkanol fatty monoester is a caprylate ester.

6. The liquid preservative composition of claim 1 wherein the alkanol fatty monoester is glyceryl caprylate.

7. The liquid preservative composition of claim 1 wherein the aqueous isothiazolinone solution is 2-methyl-4-isothiazolin-3-one at an active concentration of about 0.005 to about 55 weight percent.

8. The liquid preservative composition of claim 1 wherein the alkanol-substituted aromatic compound is phenethyl alcohol.

9. The liquid preservative composition of claim 1 wherein the alkanol-substituted aromatic compound is benzyl alcohol.

10. The liquid preservative composition of claim 1 wherein the alkanol-substituted aromatic compound is phenoxyethanol.

11. The liquid preservative composition of claim 1 wherein component (b) is a combination of phenethyl alcohol and an aqueous 2-methyl-4-isothiazolin-3-one solution.

12. The liquid preservative composition of claim 1 wherein the alkanol fatty monoester is present in the composition at a concentration in the range of about 5 to about 95 percent by weight.

13. The liquid preservative composition of claim 1 wherein component (b) is an alkanol-substituted aromatic compound present in the composition at a concentration of about 5 to about 95 percent by weight.

14. The liquid preservative composition of claim 1 wherein comprises component (b) is an aqueous solution of about 0.1 to about 25 active percent by weight of 2-methyl-4-isothiazolin-3-one.

15. The liquid preservative composition of claim 1 wherein the composition consists of about 35 to about 60 percent by weight of glyceryl caprylate and about 40 to about 65 percent by weight of phenethyl alcohol.

16. The liquid preservative composition of claim 1 wherein the composition consists of about 85 to about 95 percent by weight of glyceryl caprylate and an aqueous solution of about 0.5 to about 2 active percent by weight of 2-methyl-4-isothiazolin-3-one.

17. The liquid preservative composition of claim 1 wherein the composition is a non-aqueous composition.

18. A method of preserving a consumer or industrial product comprising admixing a preservative effective amount of the preservative composition of claim 1 with said consumer or industrial product.

19. The method of claim 18 wherein the preservative effective amount of the preservative composition is in the range of about 0.1 to about 35 percent by weight based on the combined weight of the preservative composition and said consumer or industrial product.

20. A cosmetic or personal care product comprising as the sole preservative, a preservative combination consisting of about 0.1 to about 25 percent by weight glyceryl caprylate with about 0.02 to about 10 percent by weight phenethyl alcohol and/or about 2 to about 200 ppm (active basis) of 2-methyl-4-isothiazolin-3-one; the preservative combination being free from formaldehyde, formaldehyde-releasing compounds, phenolic compounds, halogenated compounds, and paraben compounds.

21. A consumer or industrial product comprising, as the sole preservative, a preservative effective amount of the liquid preservative composition of claim 1.

* * * * *

UNITED STATES PATENT AND TRADEMARK OFFICE
CERTIFICATE OF CORRECTION

| | |
|---|---|
| PATENT NO. | : 8,367,079 B2 |
| APPLICATION NO. | : 12/812063 |
| DATED | : February 5, 2013 |
| INVENTOR(S) | : Kenneth R. Berg et al. |

It is certified that error appears in the above-identified patent and that said Letters Patent is hereby corrected as shown below:

In the Claims

In Column 10, line 50 (Claim 14, line 2), delete the word "comprises".

Signed and Sealed this
Twelfth Day of November, 2013

Teresa Stanek Rea
*Deputy Director of the United States Patent and Trademark Office*